United States Patent
Janssen et al.

(10) Patent No.: US 11,072,805 B2
(45) Date of Patent: Jul. 27, 2021

(54) TWO-PHASE FERMENTATION PROCESS FOR THE PRODUCTION OF AN ORGANIC COMPOUND

(71) Applicant: ISOBIONICS B.V., Geleen (NL)

(72) Inventors: Antonius Cornelis Johannes Matheus Janssen, Geleen (NL); Joannes Gerardus Theodorus Kierkels, Geleen (NL); Georg Friedrich Lentzen, Geleen (NL)

(73) Assignee: ISOBIONICS B.V.

( * ) Notice: Subject to any disclaimer, the term of this patent is extended or adjusted under 35 U.S.C. 154(b) by 0 days.

(21) Appl. No.: 16/257,709

(22) Filed: Jan. 25, 2019

(65) Prior Publication Data

US 2019/0225994 A1  Jul. 25, 2019

Related U.S. Application Data

(63) Continuation of application No. 14/902,707, filed as application No. PCT/NL2014/000020 on Jul. 4, 2014, now abandoned.

(30) Foreign Application Priority Data

Jul. 4, 2013 (EP) .................................. 13003384

(51) Int. Cl.
C12P 5/00 (2006.01)
(52) U.S. Cl.
CPC .................................. *C12P 5/007* (2013.01)
(58) Field of Classification Search
CPC ...................................................... C12P 5/007
USPC ......................................................... 435/166
See application file for complete search history.

(56) References Cited

U.S. PATENT DOCUMENTS

2010/0145116 A1   6/2010 Van Keulen et al.

FOREIGN PATENT DOCUMENTS

| EP | 2336310 A1 | 6/2011 |
| WO | WO 2011060057 A1 | 5/2011 |
| WO | 2013/090769 A2 | 6/2013 |

OTHER PUBLICATIONS

Written Opinion in International Application No. PCT/NL2014/000020 dated Jul. 10, 2014.
International Search Report in International Application No. PCT/NL2014/000020 dated Jul. 10, 2014.
Brennan, et al., Alleviating Monoterpene Toxicity Using a Two-Phase Extractive Fermentation for Bioproduction of Jet Fuel Mixtures in *Saccharomyces cerevisiae*, Biotechnology and Bioengineering, vol. 109, No. 10, Oct. 2012.
Oxford English Dictionary, Microorganism and Organism, Accessed Aug. 6, 2018, Available Online at: en.oxforddictionaries.com/definition/microorganism; and en.oxforddictionaries.com/definition/organism.
Liu, et al., "Use of n-hexadecane as an oxygen vector to improve Phaffia rhodozyma growth and carotenoid production in shake-flask cultures", *Journal of Applied Microbiology*, vol. 101, No. 5, Nov. 1, 2006, pp. 1033-1038.
Da Silva, et al. "Effect of n-dodecane on Chrypthecodinium cohnii fermentations and DHA production", *Journal of Industrial Microbiology and Biotechnology*, vol. 33, No. 6., Jun. 1, 2006, pp. 408-416.
Galaction, et al., "Enhancement of oxygen mass transfer in stirred bioreactors using oxygen-vectors 2. Propionibacterium shermanii broths", *Bioprocess and Biosystems Engineering Springer*, vol. 27, No. 4, Jul. 1, 2005, pp. 263.271.
Garcia-Ochoa et al., "Bioreactor scale-up and oxygen transfer rate in microbial processes: An overview", *Biotechnology Advances*, vol. 27, No. 2, Mar. 1, 2009, pp. 153-176.
Clarke, et al., "Enhancement and repression of the volumetric oxygen transfer coefficient through hydrocarbon addition and its influence on oxygen transfer rate in stirred tank bioreactors", *Biochemical Engineering Journal*, vol. 28, No. 3, Mar. 1, 2006, pp. 237-242.
Cascaval et al., "Comparative study on the effects of n-dodecane addition on oxygen transfer in stirred bioreactors for simulated, bacterial and yeast broths", Biochemical Engineering Journal, Vol. 31, No. 1, 2006, pp. 56-66.

*Primary Examiner* — Jennifer M. H. Tichy

(74) *Attorney, Agent, or Firm* — Faegre Drinker Biddle & Reath LLP

(57) ABSTRACT

The invention relates to a two phase fermentation process for producing an organic compound, in particular an isoprenoid and to a bioreactor comprising a two phase fermentation system for producing an organic compound.

10 Claims, 1 Drawing Sheet

TWO-PHASE FERMENTATION PROCESS FOR THE PRODUCTION OF AN ORGANIC COMPOUND

CROSS-REFERENCE TO RELATED APPLICATIONS

Figure 1:
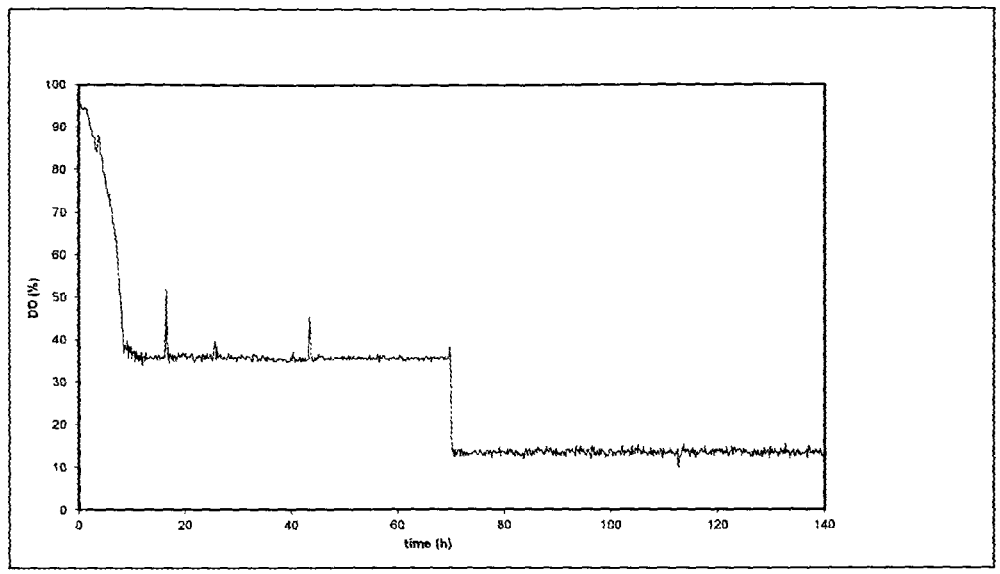

This application is a continuation of application Ser. No. 14/902,707, 371(c) date Jan. 4, 2016, which is the U.S. national phase of International Application No. PCT/NL2014/000020, filed Jul. 4, 2014 which designated the U.S. and claims priority to EP Patent Application No. 13003384.8, filed Jul. 4, 2013, each of which is incorporated herein by reference in its entirety.

The invention relates to a two phase fermentation process for producing an organic compound, in particular an isoprenoid and to a bioreactor comprising a two phase fermentation system for producing an organic compound.

Isoprenoids (also known as terpenoids or terpenes) are a large and diverse class of naturally occurring organic compounds that find potential utility, inter alia in the production of pharmaceuticals, cosmetics, perfumes, flavors, animal feed supplements and nutraceuticals.

Conventional production methods involve, e.g., extraction of these compounds from plants, microbes and animals. However, these extraction methods suffer from numerous limitations such as low yield of extraction, lack of amenability of the source organisms to large scale cultivation and complicated production methods. Also, chemical synthesis methods for producing isoprenoids are not lucrative due to the high cost of starting materials and the requirement of extensive product purification steps. In-vitro enzymatic approaches have also been explored but the exploitation of this approach is for instance restricted by the limited availability of the precursors.

Metabolic engineering of microorganisms for isoprenoid production is believed to be most promising for the production of large amounts of isoprenoids from cheap carbon sources in fermentation processes, although some hurdles still have to be taken (reviewed in Ajikumar et al, Mol. Pharmaceutics, 2008, 5 (2), 167-190). Production of isoprenoid through fermentation of microorganisms is deemed more desirable than the traditional methods as it meets the requirement of sustainable production in a more economical, industrially scalable and productive way. Production of isoprenoids via fermentation methods represents an alternate process technology that utilized lower cost of feedstock and higher productivity, affording a potential for lower cost of manufacture.

One of the most frequently encountered problems in fermentation procedures is end-product inhibition, that is, the microorganisms responsible for the fermentation may be impaired by the fermentation product, e.g. because the fermentation product is cytotoxic. Accumulation of the product beyond a critical concentration inactivates the microorganism and substantially diminishes the rate of productivity. This phenomenon is particularly relevant in the production of isoprenoids as most microbes are destroyed or inactivated in the presence of these cytotoxic compounds posing a severe limitation to obtain highly productive strains. Owing to these compounds not being obtained beyond a critical concentration, additional steps of concentration and purification may be required rendering the process cumbersome and expensive.

Another major drawback is that isoprenoids, being highly volatile organic compounds, are poorly soluble in aqueous solutions. Thus, loss of product during fermentation through the off-gas is a major problem in the development of an economically feasible process (Asadollahi et al, Biotech Bioengin 2007, 99(3): 666-677). In previous studies, terpenoids synthesized in *E. coli* were partly lost by evaporation due to their highly volatile character (Newman et al., Biotechnol. Bioeng. (2006) 95: 684-691).

To overcome the above mentioned drawbacks, attempts have been made to remove the product from the fermentation medium as the fermentation advances such that the product concentration does not rise to a point where product biosynthesis is inhibited, thus ensuring a sustained period of high rate of productivity. One such attempt utilizes a liquid that is immiscible with the aqueous fermentation medium but is an extractant for the desired product. The target product partitions between the extractant and the aqueous fermentation medium when the two are brought into contact, thereby reducing the concentration of the product in the aqueous medium. In-situ separation of the released product being performed in a two-phase fermentation using an organic solvent as the secondary phase has been attempted to mitigate the drawbacks of conventional fermentation methods. (Malinowski, Biotech Advances 2001, 19: 525-538).

In practice, two-phase extractive fermentation systems are complex owing to the unpredictable nature of these systems, particularly for large scale production. One of the most significant challenges is the selection of the right solvent system for a given product/microorganism combination. A frequently encountered difficulty, for instance is that most common water-immiscible solvents are toxic to the microorganisms and/or hazardous rendering them unsuitable for commercial scale production of products such as isoprenoids via fermentation. It has also been encountered that certain solvents form stable emulsions with the aqueous fermentation medium causing difficulties of separation, equipment blockage etc. The selection of a biocompatible organic carrier solvent with favorable partition coefficients is thus crucial for the implementation of an effective bioconversion in an aqueous-organic biphasic system (Cruz et al. 2004; León et al. 1998). Preferably, the solvent has other desirable carrier solvent characteristics, such as low emulsion-forming tendency, chemical, thermal, and biological stability.

Typically, addition of solvents during the fermentation process involves addition of large volumes of an organic solvent within a short time interval which, e.g., involves the risk of introducing potential contaminants into the medium. A loss of sterility of fermentation has serious consequences impacting production costs, schedules and affecting the product quality and quantity. Apart from the risk of introducing contamination, extractants seriously affect the stability of the signals from crucial probes, like e.g., pH-electrode and dissolved oxygen probe, interfering with accurate measurement of important parameters such pH and dissolved oxygen content of the medium. This is more common during the employment of organic solvents as extractants since oxygen usually has a higher solubility in organic solvents. Therefore, addition of organic solvents during fermentation has a serious impact on the accurate measurement of crucial parameters such as pH and dissolved oxygen that are required to control the fermentation.

These limitations have hindered the possibilities of using water-immiscible solvents during fermentation for industrial scale production of the target products. There is thus a need for an industrially scalable fermentation process for the production of organic compounds, in particular isoprenoids in the presence of a water-immiscible solvent. Further, there is a need to produce these compounds with a good yield and productivity with a low tendency to build up toxic levels of metabolic intermediates.

It is therefore an objective of the present invention to provide a fermentation method for producing organic compounds, in particular isoprenoids, that fulfills this need. It is one objective of the present invention to specifically address the challenges associated with utilization of water-immiscible solvents in industrial scale fermentation process.

It is a particular objective of the present invention to provide an industrially scalable and robust method for the production of organic compounds which permits the utilization of organic solvents as an extractant.

It is a further objective of the present invention to provide an efficient fermentation process for the industrial scale production of an organic compound, preferably an isoprenoid, employing a liquid-liquid two phase system for sustained period of high productivity.

It has now been found that this objective can be realized by adding a water-immiscible organic solvent to an aqueous medium for culturing cells to form a two phase system. An optimized ratio of the water-immiscible organic solvent to aqueous medium facilitates the selective extraction of the target compound into specific organic extractants during fermentation.

As described, the industrial scale fermentation process is in particular suited to be used for the production of an isoprenoid, as it aims at solving the problems generally associated with these highly volatile and cytotoxic compounds. However, the process is equally well suited to be used for the production of other organic compounds that possess similar process challenges.

Accordingly, the present invention provides for a two-phase fermentation process for the production of an organic compound comprising the steps of:

a) adding a water-immiscible organic solvent to an aqueous medium for culturing cells to form a two phase system, the ratio of water-immiscible organic solvent to aqueous medium being optimized and the total volume of solvent and medium is at least 10 L;

b) providing the two phase system with an oxygen probe; then c) performing a calibration of said oxygen probe; then d) optimizing oxygen tension in said two phase system; then e) inoculating said two phase system with a microorganism capable of producing said organic compound in said oxygen optimized two phase system; then f) measuring and optimizing oxygen tension; and g) allowing said microorganism to produce said organic compound.

Herein, the term "water-immiscible" refers to the nature of an organic solvent or organic solvent mixture being incapable or substantially incapable of mixing with the aqueous fermentation medium. For the purpose of this invention, water-immiscible refers to solvents where a significant proportion of the solvent does not form a solution in water. A suitable water-immiscible solvent is characterized by a high log P value (Schewe et al, Appl Microbiol Biotechnol (2009) 83:849-857). The water immiscible solvent preferably has a log P value >3, preferably a log P value >4, more preferably a log P value >4.5, most preferably a log P value >5.

For the purpose of the invention, the term "biphasic fermentation medium" or "two phase fermentation medium" is meant to include a two-phase medium comprising a fermentation medium with the aqueous medium forming an aqueous phase and a suitable amount of a water-immiscible organic solvent forming an organic phase.

In one particular embodiment, the calibration of the dissolved oxygen electrode referred to under point c) is carried out as follows: in a first step, a zero current measurement is performed by using zeroing gel or nitrogen (N2) or carbon dioxide (CO2) calibration gases, alternatively in a sample medium saturated with one of these gases. The probe is then mounted into the fermenter and autoclaved, dodecane is added and the 100% value is determined (second calibration step) after saturating with air. In this particular embodiment, the oxygen probe is thus provided to the fermenter before addition of the solvent. After addition of the solvent and saturation of the two-phase system with air, the calibration to 100% dissolved oxygen is performed.

In another particular embodiment, a two point calibration is performed in the two-phase system. A first calibration step is performed in the two-phase system which is depleted of oxygen (calibration to 0% dissolved oxygen). After saturation of the two-phase system with air, the second calibration step to 100% dissolved oxygen is performed.

The term "aqueous phase" typically relates to the phase of a biphasic system comprising the aqueous fermentation medium which is formed by its contact with the organic phase. A system is considered aqueous if water is the only solvent or the predominant solvent (>50 wt. %, preferably >80 wt. %, more preferably >90 wt. ° 10, based on total liquids), wherein e.g. a minor amount of alcohol or another solvent (<50 wt. %, preferably <20 wt. %, more preferably <10 wt. %, based on total liquids) may be dissolved (e.g. as a carbon source, in case of a full fermentative approach) in such a concentration that micro-organisms which are present remain active.

The term "organic phase", typically relates to the phase of a biphasic mixture comprising the water-immiscible organic solvent which is formed upon its contact with an aqueous fermentation medium. The water-immiscible organic solvent may be any solvent. Preferred water-immiscible organic solvents are selected from the group of dodecane, lauric acid, oleic acid, n-decane, butyl stearate, olive oil, corn-oil, diisononyl phthalate (DINP), or any combination thereof. These solvents are particularly preferred as they are substantially non-toxic to most industrially employed micro-organisms under the process conditions, tend not to form stable emulsions, have good partition coefficients for common fermentation products, and can be separated from these compounds relatively inexpensively. Hence they possess all the features imperative to render the fermentation viable on an industrial scale. In a particular preferred embodiment, the water-immiscible organic solvent is dodecane.

In principle, the production of the isoprenoid can be carried out in a manner based on methodology known per se, e.g. as described in the prior art mentioned herein above. The host cell may be used in a fermentative production of the isoprenoid, or it may be used to produce a monoterpene synthase or sesquiterpene synthase, which can thereafter then be used for synthesis of the desired terpenoid.

Advantageously, the isoprenoid is produced in a fermentative process, i.e. in a method comprising cultivating a host cell in a culture medium under conditions wherein typically a monoterpene synthase or sesquiterpene synthase is expressed. The actual reaction catalyzed by the monoterpene synthase or sesquiterpene synthase typically takes place intracellular.

It should be noted that the term "fermentative" is used herein in a broad sense for processes wherein use is made of a culture of an organism to synthesize a compound from a suitable feedstock (e.g. a carbohydrate, an amino acid source, a fatty acid source). Thus, fermentative processes as meant herein are not limited to anaerobic conditions, and extended to processes under aerobic conditions. Suitable feedstocks are generally known for host cells. Suitable conditions can be easily found using routine experimentation, using general knowledge, the present patent application and, optionally, other known methodology as, e.g., for *Rhodobacter* host cells described in WO 2011/074954 (in particular page 68, examples, general part, shake-flask procedure) which is incorporated herein by reference.

In principle, the pH of the reaction medium (culture medium) used in a method according to the invention may be chosen within wide limits, as long as it is compatible with the host cell and the isoprenoid synthase (in the host cell) is active and displays a wanted specificity under the pH conditions. The pH is preferably selected such that the cells are capable of performing their intended function or functions. The pH may in particular be chosen within the range of four pH units below neutral pH and two pH units above neutral pH, i.e. between pH 3 and pH 9 in case of an essentially aqueous system at 25° C. Good results have e.g. been achieved in an aqueous reaction medium having a pH in the range of 6.8 to 7.5.

In particular in case a yeast and/or a fungus is used, acidic conditions may be preferred, in particular the pH may be in the range of pH 3 to pH 8, based on an essentially aqueous system at 25° C. If desired, the pH may be adjusted using an acid and/or a base or buffered with a suitable combination of an acid and a base.

Microorganisms often need high levels of oxygen for effective aerobic growth. On the other hand, exposure to high oxygen levels can pose oxidative stress upon microorganisms, leading to low productivity and growth. Therefore it is often necessary to carefully control the level of dissolved oxygen in the fermentation broth. For *Rhodobacter spaeroides*, for instance, a strain that can be used for the production of isoprenoids, it is advantageous to use high levels of oxygen saturation in an early phase of a fermentation process to generate biomass and low oxygen saturation in later stages to promote production of the isoprenoid. Therefore oxygen tension in the broth needs to be maintained at distinct levels at all times, typically between 10% and 100% saturation, preferably 20%-60% in the early phase of fermentation and 0% and 50%, preferably 0% to 25% in the later phase of the fermentation.

In a preferred embodiment, therefore, the oxygen tension (dissolved oxygen (DO)), is between 50-100%, preferably between 80-100%, more preferably about 100% at the time of inoculation. Preferably the oxygen tension is allowed to decrease to between 10-60%, preferably between 20-50%, more preferably between 30-40%, most preferably about 35% shortly after inoculation, and kept at this level during production of biomass. During production of the organic compound of interest, the dissolved oxygen tension is preferably kept between 0-50%, more preferably between 5-25%, more preferably between 10-15%, most preferably about 12.5%.

In a working example, the inventors have shown that these conditions are achieved when performing a process according to the invention. A comparable example wherein dodecane was added after inoculation shows that these conditions are not achieved and that addition of dodecane after inoculation has a negative effect on the fermentation process.

Anaerobic conditions are herein defined as conditions without any oxygen or in which substantially no oxygen is consumed by the cultured cells, in particular a micro-organism, and usually corresponds to an oxygen consumption of less than 5 mmol/l·h, preferably to an oxygen consumption of less than 2.5 mmol/l·h, or more preferably less than 1 mmol/l·h. Aerobic conditions are conditions in which a sufficient level of oxygen for unrestricted growth is dissolved in the medium, able to support a rate of oxygen consumption of at least 10 mmol/l·h, more preferably more than 20 mmol/l·h, even more preferably more than 50 mmol/l·h, and most preferably more than 100 mmol/l·h.

Oxygen-limited conditions are defined as conditions in which the oxygen consumption is limited by the oxygen transfer from the gas to the liquid. The lower limit for oxygen-limited conditions is determined by the upper limit for anaerobic conditions, i.e. usually at least 1 mmol/l·h, and in particular at least 2.5 mmol/l·h, or at least 5 mmol/l·h. The upper limit for oxygen-limited conditions is determined by the lower limit for aerobic conditions, i.e. less than 100 mmol/l·h, less than 50 mmol/l·h, less than 20 mmol/l·h, or less than to 10 mmol/l·h.

Whether conditions are aerobic, anaerobic or oxygen-limited is dependent on the conditions under which the method is carried out, in particular by the amount and composition of ingoing gas flow, the actual mixing/mass transfer properties of the equipment used, the type of micro-organism used and the micro-organism density.

In principle, the temperature used is not critical, as long as the isoprenoid synthase (in the cells), shows substantial activity. Generally, the temperature is at least 0° C., in particular at least 15° C., more in particular at least 20° C. A desired maximum temperature depends upon the isoprenoid synthase and the host cell used. Depending on the cells and/or the isoprenoid synthase used, the temperature is 70° or less, preferably 50° C. or less, more preferably 40° C. or less, in particular 37° C. or less. Organisms like *Thermus thermophilus* have a temperature optimum for growth between 49° C. and 72° C., *Escherichia coli* of about 37° C., and many fungal microorganisms like yeasts and bacterial microorganisms like *Rhodobacter spaeroides* have temperature optima around 30° C. In case of a fermentative process, the incubation conditions can be chosen within wide limits as long as the cells show sufficient activity and/or growth. This includes pH ranges, temperature ranges and aerobic, oxygen-limited and/or anaerobic conditions.

In one embodiment of the invention, the water-immiscible organic solvent is introduced in the aqueous medium in an amount effective to facilitate the in-situ extraction of the produced organic compound into the organic phase and to increase the rate and/or yield of its production by the micro-organism in the aqueous phase. According to a preferred embodiment of the invention, the ratio of water-immiscible organic solvent to aqueous medium is between 0.5% (v/v) and 60% (v/v), preferably between 2% (v/v) and 40% (v/v) and more preferably between 5% (v/v) and 20% (v/v).

A solvent to be utilized as an extractant in a process according to the invention preferably meet the following requirements for use in a commercial two-phase extractive fermentation process: low solubility in water, non-toxic to the producing microorganism, large partition co-efficient for the product, low partition-coefficient for nutrients, high selectivity, low emulsion forming tendency, high chemical and thermal stability, non-biodegradability, non-hazardous and/or low cost.

In particular suitable (for extraction from an aqueous reaction medium) is extraction with a liquid organic solvent, such as a liquid hydrocarbon. From initial results it is apparent that this method is also suitable to extract the isoprenoid (or further product) from a reaction medium comprising cells according to the invention used for its production, without needing to lyse the cells for recovery of the isoprenoid (or further product). In particular, the organic solvent may be selected from liquid alkanes, liquid long-chain alcohols (alcohols having at least 12 carbon atoms), and liquid esters of long-chain fatty acids (acids having at least 12 carbon atoms). Suitable liquid alkanes in particular include C6-C16 alkanes, such as hexane, octane, decane, dodecane, isododecane and hexadecane. Suitable long-chain aliphatic alcohol in particular include C12-C18 aliphatic alcohols, like oleyl alcohol and palmitoleyl alcohol. Suitable esters of long-chain fatty acids in particular include esters of C1-C4 alcohols of C12-C18 fatty acids, like isopropyl myristate, and ethyl oleate In an advantageous embodiment, isoprenoid (or a further product) is produced in a reactor comprising a first liquid phase (the reaction phase), said first liquid phase containing cells according to the invention, wherein the isoprenoid (or a further product) is produced, and a second liquid phase (organic phase that remains essentially phase-separated with the first phase when contacted), said second liquid phase being the extracting phase, for which the formed product has a higher affinity. This method is advantageous in that it allows in situ product recovery. Also, it contributes to preventing or at least reducing potential toxic effects of isoprenoid (or a further product) to the cells, because due to the presence of the second phase, the isoprenoid (or a further product) concentration in the reaction phase may be kept relatively low throughout the process. Finally, the extracting phase contributes to extracting the isoprenoid (or further product) out of the reaction phase.

In a preferred method of the invention the extracting phase forms a layer on top of the reaction phase or is mixed with the reaction phase to form a dispersion of the reaction phase in the extracting phase or a dispersion of the extracting phase in the reaction phase. Thus, the extracting phase not only extracts product from the reaction phase, but also helps to reduce or completely avoid losses of the formed product from the reactor through the off-gas, that may occur if isoprenoid is produced in the (aqueous) reaction phase or excreted into the (aqueous) reaction phase. Isoprenoid is poorly soluble in water and therefore easily volatilizes from water. It is contemplated that isoprenoid solvated in the organic phase (as a layer or dispersion) is at least substantially prevented from volatilization.

Suitable liquids for use as extracting phase combine a lower density than the reaction phase with a good biocompatibility (no interference with the viability of living cells), low volatility, and near absolute immiscibility with the aqueous reaction phase. Examples of suitable liquids for this application are liquid alkanes like decane, dodecane, isododecane, tetradecane, and hexadecane or long-chain aliphatic alcohols like oleyl alcohol, and palmitoleyl alcohol, or esters of long-chain fatty acids like isopropyl myristate, and ethyl oleate (see e.g. Asadollahi et al. (Biotechnol. Bioeng. (2008) 99: 666-677), Newman et al. (Biotechnol. Bioeng. (2006) 95: 684-691) and WO 2009/042070). In a preferred embodiment, a process according to the invention is provided, wherein the water-immiscible organic solvent is a liquid alkane or a long-chain aliphatic alcohol or an ester of a long-chain fatty acid or an isoprenoid. In a preferred embodiment, the organic solvent is dodecane, lauric acid, oleic acid, n-decane, butyl stearate, olive oil, corn oil or DINP, most preferably dodecane.

In a process of the invention, the water-immiscible organic solvent is added prior to the start of the fermentation, i.e. before inoculating the two phase system with a microorganism capable of producing the organic compound. It is an advantage to add the solvent before the initiation of fermentation since introducing the solvent during fermentation carries the risk of introducing contaminants into the medium which could be detrimental to the outcome of the fermentation process. Additionally, oxygen has a higher solubility in organic solvents which complicates the accuracy of the measurement if the solvents are added afterwards. Therefore, addition of organic solvents during fermentation bears a crucial impact on the accurate measurement of operational parameters such as pH and dissolved oxygen required to control the fermentation. One additional advantage is that the point in time of introducing the solvent in a conventional method is dictated by the fermentation process.

If desired, isoprenoids produced in a method according to the invention, or a further compound into which isoprenoid has been converted after its preparation (such as nootkatone), is recovered from the reaction medium, wherein it has been made. A suitable method is liquid-liquid extraction with an extracting liquid that is non-miscible with the reaction medium.

A particular strategy of conducting the fermentation is by adding the organic solvent prior to the start of the fermentation, enabling in-situ sterilization of the medium and solvent in the absence of the producing microorganism. The concurrent sterilization of the two phases further evades the need for multiple sterilization steps of the individual phases. In addition, the calibration of the crucial probes such as the oxygen probe must be undertaken in the presence of the organic solvent. Therefore, the oxygen probe must be suitable for measuring oxygen tension in the two phase system, thus in the presence of the organic solvent. By adding the solvent beforehand and optimizing the oxygen tension in the two-phase system, the disadvantages associated with the interim addition of the solvent during fermentation are circumvented. In a preferred embodiment, the invention provides a process according to the invention, wherein the process further comprises sterilizing the two phase system prepared in step a), preferably by sterilizing the two phase system at at least 1 bar overpressure for at least 20 minutes at at least 120° C., preferably between 20-40 minutes at about 121° C. at at least 1 bar overpressure. Preferably the sterilization step takes place before step e), more preferably before step c). In one particular embodiment, instead of sterilizing the two phase system, sterile medium is used as the aqueous phase, typically sterilized before or after adding the medium to the bioreactor, and sterile solvent is added thereto. It is possible to add sterile solvent for instance by passing the solvent through a sterilization filter (e.g. a 0.22 μm filter) or by using pre-sterilized solvent. Methods for adding a solvent to an aqueous phase, such that the resulting two-phase system remains sterile are known in the art.

For the purpose of the invention, the terms "fermentation medium" and "medium" are meant to include the liquid medium in which the microorganisms are grown. In a particular embodiment it is preferred to use a semisolid medium. A typical fermentation medium commonly includes a substrate and nutrients. The fermentation medium additionally contains the microorganism, the product produced by the microorganism, metabolic intermediates and other components such as salts, vitamins, amino acids, co-factors and antibiotics. Substrates are commonly sugars or more complex carbohydrates that are metabolized by the microorganism to obtain energy and basic structural components, but can also be lipids and/or proteins.

The two-phase fermentation process of the present invention is particularly suitable for the industrial scale production of an organic compound, preferably an isoprenoid. Accordingly, in a preferred embodiment of the invention, the total volume of the solvent and medium is at least 30 L, preferably at least 100 L, more preferably at least 1,000 L, more preferably at least 10,000 L, most preferably at least 30,000 L or more.

In a preferred embodiment, a process according to the invention is provided, wherein the organic compound is an isoprenoid. Herein, the term "isoprenoid" refers to a large and diverse class of naturally occurring organic compounds typically composed of two or more units of hydrocarbons, with each unit consisting of five carbon atoms arranged in a specific pattern. Isoprenoids are built from isoprene units (2-methyl-1,3-butadiene) and the biological precursor for all natural isoprenoids is isopentenyl diphosphate (IPP). Isoprene (2-methyl-1,3 butadiene is a branched-chain unsaturated hydrocarbon. Non-limiting examples of suitable isoprenoids include hemiterpenes (derived from a single isoprene unit) such as isoprene, monoterpenes (derived from two isoprene units) such as mycrene, sesquiterpenes (derived from three isoprene units) such as amorpha-4,11-diene, diterpenes (derived from four isoprene units) such as taxadiene, triterpenes (derived from six isoprene units) such as squalene, tetraterpenes (derived from eight isoprene units) such as 3-carotene and polyterpenes (derived from more than eight isoprene units) such as polyisoprene or a mixtures of these. Terpenoids are also included as terpenes for the purposes of the present invention. In a particular preferred embodiment, the isoprenoid is a monoterpene or a sesquiterpene, diterpene or triterpene, more preferably a monoterpene or iridoid selected from the group consisting of Ascaridole, Bornane, Borneol, Camphene, Camphor, Cantharidin, Carene, Carvacrol, Carveol, Carvone, Carvonic acid, Chrysanthemic acid, Chrysanthenone, Citral, Citronellal, Citronellol, Cuminaldehyde, P-Cymene, Cymenes, Epomediol, Eucalyptol, Fenchol, Fenchone, Geranic acid, Geraniol, Geranyl acetate, Grapefruit mercaptan, Halomon, Hinokitiol, (S)-Ipsdienol, Levoverbenone, Limonene, Linalool, Linalyl acetate, Lineatin, P-Menthane-3,8-diol, Menthofuran, Menthol, Menthone, Menthoxypropanediol, Menthyl acetate, 2-Methylisoborneol, Myrcene, Myrcenol, Nerol, Ocimene, Perilla ketone, Perillaldehyde, Perillartine, Phellandrene, Picrocrocin, Pinene, Alpha-Pinene, Beta-Pinene, Piperitone, Pulegone, Rhodinol, Rose oxide, Sabinene, Safranal, Sobrerol, Terpinen-4-ol, Terpinene, Terpineol, Thujaplicin, Thujene, Thujone, Thymol, Thymoquinone, Umbellulone, and Verbenone, and/or a sesquiterpene or a sesquiterpene lactone selected from the group consisting of Abscisic acid, Amorpha-4,11-diene, Andrographolide, Aristolochene, Artemether, Artemotil, Artesunate, Bisabolene, Bisabolol, Botrydial, Cadalene, Cadinene, Alpha-Cadinol, Delta-Cadinol, Capnellene, Capsidiol, Carotol, Caryophyllene, Cedrene, Cedrol, Copaene, Cubebol, Elemene, Farnesene, Farnesol, Furanolactone, Germacrene, Guaiazulene, Guaiene, Guaiol, Gyrinal, Hernandulcin, Humulene, Illudin, Indometacin farnesil, Isocomene, Juvabione, Longifolene, Mutisianthol, Nerolidol, Nootkatone, Norpatchoulenol, Onchidal, Patchoulol, Periplanone B, Petasin, Phaseic acid, Polygodial, A-Santalol, B-Santalol, Santonic acid, Selinene, Sterpuric acid, Thujopsene, Valencene, Velleral, Verrucarin A, Vetivazulene, A-Vetivone, and Zingiberene, and/or a diterpene, a pleuromutilin or a taxane selected from the group consisting of Abietane, Abietic acid, Agelasine, Aphidicolin, Beta-Araneosene, Bipinnatin J, Cafestol, Carnosic acid, Cembrene A, 10-Deacetylbaccatin, Ferruginol, Fichtelite, Forskolin, Galanolactone, Geranylgeraniol, Gibberellin, Ginkgolide, Grayanotoxin, Guanacastepene A, Ingenol mebutate, Isocupressic acid, Isopimaric acid, Kahweol, Labdane, Lagochilin, Leelamine, Levopimaric acid, Menatetrenone, Momilactone B, 18-Norabietane, Paniculidine, Phorbol, Phorbol 12,13-dibutyrate, Phytane, Phytanic acid, Phytol, Pimaric acid, Pristane, Pristanic acid, Prostratin, Pseudopterosin A, Quassin, Retinol, Sclarene, Sciareol, Simonellite, Stemarene, Stemodene, Steviol, Steviol glycoside, Taxodone, 12-O-Tetradecanoylphorbol-13-acetate, Tetrahydrocannabinol-C4, Tetrahydrocannabinolic acid, Totarol, and Triptolide, and/or a triterpene selected from the group consisting of Absinthin, Acetoxolone, Aescin, Ambrein, Amyrin, Balsaminapentaol, Balsaminol A, Balsaminol B, Betulin, Betulinic acid, Bevirimat, Boswellic acid, Bryoamaride, Carbenoxolone, Celastrol, Corosolic acid, Cucurbalsaminol A, Cucurbalsaminol B, Cucurbitane, Cycloartenol, Cycloastragenol, Dammarane, Endecaphyllacin, Ganoderic acid, Ginsenoside, Glycyrrhetinic acid, Glycyrrhizin, Hederagenin, Hemslecin, Hopane, Hopanoids, Karavilagenin E, Lanostane, Lanosterol, Lepidolide, Lupeol, Malabaricane, Maslinic acid, Momordicilin, Momordicin I, Momordicin-28, Momordicinin, Moronic acid, Neokuguaglucoside, Oleanane, Oleanolic acid, 2,3-Oxidosqualene, Panaxatriol, Perseapicroside, Protopanaxadiol, Protopanaxadiol, Sapogenin, Squalane, Squalene, Tetranortriterpenoid, Triterpenoid saponin, Ursolic acid, and Yamogenin.

According to a preferred embodiment of the invention, said micro-organism, when cultivated in said aqueous phase is capable of producing said isoprenoid in an amount sufficient to reach a saturated concentration thereof in said aqueous phase.

The present fermentation processes are useful with almost any type of microorganism used for fermentation. The microorganism could be any microorganism that is capable of producing an organic compound, preferably an isoprenoid. By way of example, the microorganism can be a yeast, bacteria, fungi, or a mixture of any of these. In a particular preferred embodiment, the microorganism is optimized for production of said organic compound, for instance by genetic modifications.

In a particular preferred embodiment, the microorganism is a bacterium or a fungal or a plant cell. In a preferred embodiment, the microorganism is a bacterial cell selected from the group of Gram negative bacteria, such as *Rhodobacter, Agrobacterium, Paracoccus,* or *Escherichia;* a bacterial cell selected from the group of Gram positive bacteria, such as *Bacillus, Corynebacterium, Brevibacterium;* a fungal cell selected from the group of *Aspergillus, Blakeslea, Penicillium, Phaffia (Xanthophyllomyces), Pichia, Saccharamoyces, Yarrowia,* and *Hansenula;* a transgenic plant or culture comprising transgenic plant cells, wherein the microorganism is of a transgenic plant selected from *Nicotiana* spp, *Cichorum intybus, Iacuca sativa, Menthe* spp, *Artemisia annua,* tuber forming plants, oil crops and trees; or a transgenic mushroom or culture comprising transgenic mushroom cells, wherein the microorganism is selected from *Schizophyllum, Agaricus* and *Pleurotisi*. In a most preferred embodiment, the microorganism is a *Rhodobacter sphaeroides* bacterium.

In one embodiment, a process according to the invention is provided, wherein the process further comprises the isolation of the organic compound from the two phase system. As the organic compound preferably accumulates in the water-immiscible organic solvent, the organic compound is preferably isolated from said organic solvent. Extraction methods of organic compounds are known by the skilled person and include, but are not limited to liquid-liquid extractions, distillation, pervaporation, etc. In a preferred embodiment, the organic compound is extracted by pervaporation. Pervaporation is a membrane technical method for the separation of mixtures of liquids by partial vaporization through a non-porous or porous membrane. It is preferred that before the organic compound is isolated, the microorganism is allowed to produce said organic compound for a sufficient amount of time, preferably for at least 2 days and not more than 7 days.

The process may be performed in a batch mode, in a fed-batch mode or in a continuous mode. The terms "batch mode", "fed-batch mode" and "continuous mode" are known to one skilled in the art. A process according to the invention can easily be performed such that it is run in a batch mode, fed-batch mode or continuous mode.

The invention further provides a bioreactor, which is a vessel or a device for containing medium and for carrying out a fermentation process. The bioreactor is capable of carrying out a two phase fermentation process of the invention and preferably is capable of providing the optimum growth conditions for the microorganism.

In one embodiment, the invention provides a bioreactor comprising at least 10 L of a two phase system comprising a water-immiscible organic solvent and an aqueous medium for culturing cells, wherein the ratio of water-immiscible organic solvent to aqueous medium is between 0.5% (v/v) and 60%, preferably between 2% (v/v) and 40% (v/v), more preferably between 5% (v/v) and 20% (v/v), most preferably between 10% (v/v) and 20% (v/v). The bioreactor may be of any shape, generally tubular, suitably may be a cylindrical shaped vessel. it is desirable that the bioreactor is made of a material that is inert to the two-phase medium, for example stainless steel or a suitably lined metallic vessel, or optionally an inert plastic material.

The design of the bioreactor could be of batch-type or fed-batch type. The bioreactor of the invention preferably comprises the major portions that include a vessel comprising a reaction port and a harvesting port.

In a preferred embodiment, the bioreactor comprises at least 30 L, more preferably at least 100 L, more preferably at least 1000 L, most preferably at least 10000 L of a two phase system comprising a water-immiscible organic solvent and an aqueous medium for culturing cells.

The bioreactor preferably comprises a means for introducing the aqueous medium into the vessel and means for introducing the water-immiscible organic solvent for contact with the aqueous medium to form a two-phase system. Such water-immiscible organic solvents are selected from the group consisting of dodecane, lauric acid, oleic acid, n-decane, butyl stearate, olive oil, corn oil, and DINP, or any combination thereof.

Because the bioreactor according to the invention is intended for producing an organic compound, preferably an isoprenoid, using a process according to the invention, in a preferred embodiment, the bioreactor according to the invention, further comprises a microorganism capable of producing an organic compound. Preferably said organic compound is an isoprenoid.

In order to measure oxygen tension, pH and temperature in the two-phase system present in said bioreactor, in a preferred embodiment, a bioreactor according to the invention further comprises one or more probes, capable of measuring these parameters in the two phase system. The bioreactor according to the invention preferably comprises at least one probe capable of measuring oxygen (oxygen probe).

In one particular embodiment, an organic solvent is present in said bioreactor. Preferably, the organic solvent is a liquid alkane or a long-chain aliphatic alcohol or an ester of a long-chain fatty acid or an isoprenoid, preferably selected from the group consisting of dodecane, lauric acid, oleic acid, n-decane, butyl stearate, olive oil, corn oil and DINP. In a most preferred embodiment, the organic solvent is dodecane.

Preferably the microorganism present in said bioreactor is:

a bacterial cell selected from the group of Gram negative bacteria, such as *Rhodobacter, Agrobacterium, Paracoccus*, or *Escherichia*;

a bacterial cell selected from the group of Gram positive bacteria, such as *Bacillus, Corynebacterium*, or *Brevibacterium*;

a fungal cell selected from the group of *Aspergillus, Blakeslea, Penicillium, Phaffia (Xanthophyllomyces), Pichia, Saccharamoyces, Yarrowia*, and *Hansenula*;

a transgenic plant or culture comprising transgenic plant cells, wherein the microorganism is of a transgenic plant selected from *Nicotiana* spp, *Cichorum intybus, Iacuca sativa, Mentha* spp, *Artemisia annua*, tuber forming plants, oil crops and trees; or a transgenic mushroom or culture comprising transgenic mushroom cells, wherein the microorganism is selected from *Schizophyllum, Agaricus* and *Pleurotisi*. In a most preferred embodiment, the microorganism is a *Rhodobacter sphaeroides* bacterium. In a particular preferred embodiment, the microorganism is optimized for production of said organic compound, for instance by genetic modifications.

The following examples describe specific embodiments of the present invention and are not intended to limit the invention in any way.

LEGEND TO THE FIGURES

FIG. 1: Oxygen profile during fermentation of valencene in a 40 L fermenter adding n-dodecane prior to inoculation. Prior to addition of the seed culture, the oxygen electrode was carefully calibrated at 0% and 100% oxygen saturation. After inoculation, the dissolved oxygen (DO) was allowed to decrease to 35% and was kept constant thereafter. At 70 h the DO was set to 12.5% and kept constant until the end of the fermentation.

Figure 2:
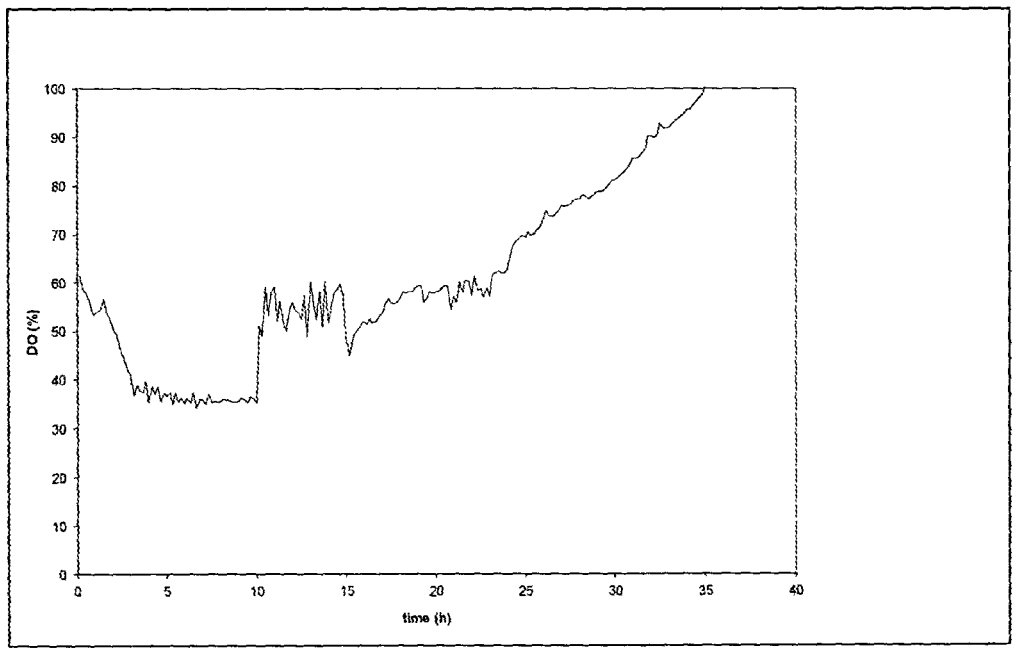

FIG. 2: Oxygen profile during fermentation of valencene in a 40 L fermenter adding n-dodecane after inoculation. Prior to addition of the seed culture, the oxygen electrode was carefully calibrated at 0% and 100% oxygen saturation. After inoculation, the dissolved oxygen (DO) was allowed to decrease to 35% and was kept constant thereafter. At 10 h after inoculation n-dodecane was slowly added, causing a rapid increase in dissolved oxygen.

EXAMPLES

Example 1: Seed Medium

TABLE 1

| Ingredient | g/L |
| --- | --- |
| Yeast extract | 20.8 |
| MgSO$_4$•7H$_2$O | 10.3 |
| ZnSO$_4$•7H2O | 0.086 |
| MnSO$_4$•H2O | 0.029 |
| CaCl$_2$•2H$_2$O | 1.08 |
| FeSO$_4$•7H$_2$0 | 0.96 |
| KH$_2$PO$_4$ | 1.44 |
| K$_2$HPO$_4$ | 1.44 | pH is adjusted to 7.0 with 5N NaOH

Components (except glucose) are dissolved in water, adjusted to pH 7 and autoclaved.

Example 2: Main Fermentation Medium

TABLE 2

| Ingredient | g/L |
| --- | --- |
| Yeast extract | 25 |
| MgSO$_4$•7H$_2$O | 1.5 |
| ZnSO$_4$•7H$_2$O | 0.1 |
| MnSO$_4$•H$_2$O | 0.03 |
| CaCl$_2$•2H$_2$O | 1.1 |
| FeCl$_3$•6H$_2$O | 0.15 |
| K$_2$HPO$_4$ | 1.5 |
| KH$_2$PO$_4$ | 1.5 |
| (NH$_4$)$_2$Fe(SO$_4$)$_2$•6H$_2$O | 1.2 |
| (NH$_4$)$_2$SO$_4$ | 2.4 |
| (NH$_4$)H$_2$PO$_4$ | 1 |
| MgCl•6H$_2$O | 1.7 |

Example 3: Two Point Calibration of the Oxygen Electrode

The fermentation medium is prepared according to recipe (Table 2) and autoclaved inside the fermenter. Sterile glucose solution is added to a final concentration of 30 g/L and neomycin (100 mg/ml) is added. Then 20 vol % of sterile n-dodecane is added. The stirrer is agitated at the maximum speed applied during fermentation run and the airflow is set to least 1 vvm (volume/volume per minute). Overpressure is kept as low as possible and constant over the fermentation run. pH and temperature are set to fermentation values. Nitrogen gas is sparged into the fermenter at 1 vvm until the reactor is fully depleted of oxygen. When the value read in the electrode is stable, that electrode value is fixed as 0%.

Alternatively, for large fermenters with volume >100 l, calibration to 0% oxygen is performed outside of the main fermenter in a small vessel and the calibrated electrode is then transferred to the main fermenter.

The main fermenter is then sparged with air at the maximal gas-flow applied during fermentation run. When the value read in the electrode is stable, that electrode value is fixed as 100%. Other fermentation parameters (pressure, air flow, rpm) are set to fermentation start point and the fermenter is inoculated with a *Rhodobacter sphaeroides* preculture with a cell density corresponding to ca. 40 OD620 nm units with an inoculation ratio of 5%.

Example 4: Comparative Example Adding n-Dodecane During Fermentation

The main fermentation was performed in a 35 m$^3$ vessel that is charged with 10000 kg medium containing 22 g/L initial glucose at a temperature of 30° C., a pH of 7.0 (controlled with 28 wt % NH$_3$ solution), an aeration of 2 Nm$^3$/min and an overpressure of 0.5 bar. At 0 hours the main fermentation was inoculated using 1 m$^3$ seed culture (see example 7). The dissolved oxygen (DO) is kept constant at 35% by adjusting the stirrer speed between 60 and 90 RPM and adjusting the aeration between 0.2 and 1.8 vvm. After 12 hours of batch fermentation the pO$_2$ value decreased strongly to a value of 15% and started to increase rapidly after that. Also the pH increase rapidly from pH 7.0 to pH 7.7. Analysis shows that all glucose was consumed and glucose feeding was started, keeping the pH at 7.0. After 26 hours 2000 L n-dodecane was slowly added to the fermenter via a sterile filter, with a dosing rate of 500 L/hour. During addition of n-dodecane it was observed that the pO$_2$ signal was very unstable and difficult to control. Finally, after all n-dodecane was added the pO$_2$ value had increased from 35% to about 80%. Regularly residual glucose checks demonstrated that the process was proceeding in glucose limitation. After about 60 hours the respiration rate started to decrease and glucose accumulation started to occur. After 78 hours glucose was no longer consumed and the concentration rapidly increased. Analysis of the valencene concentration indicated that the biomass was no longer active.

Example 5: Valencene Fermentation in a 40 L Fermenter Adding n-Dodecane Prior to Inoculation A frozen stock vial containing 1 mL of *Rhodobacter sphaeroides* valencene production strain containing genes encoding the mevalonate pathway of *Paracoccus denitrificans* and a Valencene synthase gene (see Example 9) was cultivated in a 2000 mL shake flask containing 500 mL medium as described in example 1 and an additional 100 mg/L neomycin. The shake flask was incubated on an orbital shaker at 180 rpm and an amplitude of 4 cm for 46 hours at 30° C. The culture was transferred into a 40 L stainless steel Techfors-S fermentor from Infors that containing 9 kg of medium with the following composition: 21 WI yeast extract, 1.73 g/l MgSO$_4$.7H$_2$O, 0.104 g/l ZnSO$_4$.7H$_2$O, 0.035 g/l MnSO$_4$.H$_2$O, 1.3 g/l CaCl$_2$.2H$_2$O, 1.73 g/l KH$_2$PO$_4$, 1.73 g/l K$_2$HPO$_4$, 33 g/l dextrose, 1.2 g/l (NH$_4$)$_2$Fe(SO$_4$)$_2$.6H$_2$O, 0.17 g/l FeCl$_3$.6H$_2$O, 2.76 g/l (NH$_4$)$_2$SO$_4$, 0.94 g/l (NH$_4$)H$_2$PO$_4$, 1.6 g/l MgCl.6H$_2$O and 125 g/l n-dodecane. Prior to addition of the seed culture the medium was sterilized, adjusted to pH 7 with NH$_4$OH 25 wt % and the oxygen electrode was carefully calibrated at 0% and 100% oxygen saturation, according to the procedure described in example 2. After inoculation the fermentation runs in batch mode at 30° C. and pH at 7.0 for 16.5 hours, allowing the DO to decrease initially to 35% and keeping in constant thereafter. After this batch phase the glucose feed is started by adding 17.2 kg of a solution containing 55 wt % glucose. During this phase the pH was kept constant at 7.0 and the DO at 35%. At 70 hours the pO$_2$ setpoint was put on 12.5% and kept constant until the end of fermentation by adjusting the stirrer speed. The oxygen profile during fermentation was recorded and is presented in FIG. 1.

Example 6: Comparative Example Valencene Fermentation in a 40 L Fermenter

The experiment described in example 5 was repeated except that the medium of the main fermentation did not contain n-dodecane. After preparation, sterilization and cooling of the medium the oxygen electrode was carefully calibrated at 0% and 100% oxygen saturation. The fermenter was then inoculated by adding 500 ml of a seed culture prepared according to the procedure described in example 4 and run in batch mode at 30° C. and pH 7.0 for about 10 hours, allowing the DO to decrease to 35%. At 10 hours after inoculation the glucose feed was started, followed by the slow addition of 1500 ml n-dodecane via a sterile filter, with a dosing rate of 400 ml/hour. After adding the n-dodecane the DO rapidly increased as shown in FIG. 2. Analysis of the residual glucose showed that after about 20 hours of fermentation glucose started to accumulate. Analysis of the amount of biomass indicated that cell growth had stopped.

Example 7: Seed Culture

A 2500 L fermenter is charged with 1000 kg seed medium. The medium composition is shown in table 1. After sterilization at 121° C. for 30 minutes, neomycin is added via a sterile filter to a final concentration 100 mg/kg and 68 kg 55 wt % glucose. Next, the oxygen probe is calibrated followed by inoculation of the fermentor with 500 mL of a cell culture. The fermentation is operated in batch mode for 48 hours at 30° C., pH 7.0 using 25 wt % $NH_3$ solution, an aeration of 1 vvm, an overpressure of 0.3-0.4 bar, and an DO of 35%. The DO is kept constant by agitation.

Example 8: Main Fermentation Adding n-Dodecane Prior to Inoculation

The main fermentation runs in fed-batch mode using a 35 $m^3$ vessel that is charged with 10000 kg medium. The medium composition is shown in table 2. To prepare 10000 kg of medium, medium components are dissolved in water, sterilized by autoclaving at 121° C. for 30 minutes in the bioreactor.

After sterilization and cooling of the medium the pH is adjusted to 7 with $NH_4OH$ 25%. After sterilization 600 kg 55 wt % glucose is added. Next 2000 L (1666 kg) n-dodecane is added via a sterile filter. The oxygen probe is calibrated (see example 3). The fermentation starts by adding 1000 L culture obtained from a seed. After inoculation the fermentation runs in batch mode at 30° C. and pH at 7.0 for 20 hours, keeping the DO at 35%. The OD is kept constant at 35% by adjusting the stirrer speed between 60 and 90 RPM and adjusting the aeration between 0.2 and 1.8 vvm. After 20 hours the glucose feed is started, keeping the pH at 7.0 and the DO at 35%. At 70 hours the $pO_2$ setpoint was put on 12.5% and kept constant until the end of fermentation by adjusting the stirrer speed. The fed-batch mode runs for approximately 120 hours at 30° C. and pH at 7.0.

Regularly residual glucose checks demonstrated that the process was proceeding in glucose limitation. The respiration rate remained high over the whole course of the fermentation and no glucose accumulation was observed. Analysis of the valencene concentration showed that the biomass was still producing valencene 140 h after inoculation.

Example 9: Valencene Producing *Rhodobacter* Strain

*Rhodobacter sphaeroides* strain Rs265-9c was obtained from *Rhodobacter sphaeroides* strain ATCC 35053 [purchased from the American Type Culture Collection (ATCC—Manassas, Va., USA—www.atcc.org); number 35053; *Rhodobacter sphaeroides* (van Niel) Imhoff et al., isolated from a sewage settling pond in Indiana and deposited as *Rhodopseudomonas sphaeroides* van Niel] after two rounds of mutagenesis and was used as the base host for construction of recombinant strains having improved production of isoprenoid. For details about this strain, see WO20110749654, which is incorporated herein by reference.

The invention claimed is:

1. A two-phase fermentation process for the production of an organic compound, comprising the steps of:
    a) adding a water-immiscible organic solvent to an aqueous medium for culturing cells to form a two phase system, wherein the ratio of water-immiscible organic solvent to aqueous medium is between 0.5 v/v % and 60 v/v % and the total volume of solvent and medium is at least 10 L;
    b) providing the two phase system with an oxygen probe; then
    c) performing a calibration of said oxygen probe; then
    d) optimizing oxygen tension in said two phase system, wherein the optimized oxygen tension is between 50-100%; then
    e) inoculating said two phase system with a microorganism capable of producing said organic compound in said oxygen optimized two phase system; then
    f) measuring and optimizing oxygen tension to between 10-60%; and
    g) allowing said microorganism to produce said organic compound at an optimized oxygen tension of between 0-50%.

2. Process according to claim 1, wherein the total volume of solvent and medium is at least 30 L.

3. Process according to claim 1, wherein the process further comprises sterilizing the two phase system prepared in step a), wherein the sterilization takes place before step e).

4. Process according to claim 1, wherein the process further comprises isolation of the organic compound from the two phase system.

5. Process according to claim 1, wherein the water-immiscible organic solvent is a liquid alkane or a long-chain aliphatic alcohol or an ester of a long-chain fatty acid.

6. Process according to claim 1, wherein the water-immiscible organic solvent is dodecane, lauric acid, oleic acid, n-decane, butyl stearate, olive oil, corn oil or DINP.

7. Process according to claim 1, wherein the microorganism is a Gram positive bacterial cell, a Gram negative bacterial cell, a fungal cell, or a culture comprising a transgenic plant cell.

8. Process according to claim 1, wherein the percentage of water-immiscible organic solvent in the two-phase system is between 2 v/v % and 40 v/v %.

9. Process according to claim 1, wherein the organic compound is an isoprenoid.

10. Process according to claim 1, wherein the organic compound is a monoterpene, a sesquiterpene, a diterpene or a triterpene.

* * * * *